United States Patent [19]

Reiter et al.

[11] Patent Number: 5,266,721
[45] Date of Patent: Nov. 30, 1993

[54] PROCESS FOR PREPARING THE PURE ENANTIOMERS OF LIFIBROL AND ITS ALKYL ESTERS

[75] Inventors: Friedemann Reiter, Putzbrunn; Hans-Helmut Henschel, Munich, both of Fed. Rep. of Germany

[73] Assignee: Klinge Pharma GmbH, Munich, Fed. Rep. of Germany

[21] Appl. No.: 894,298

[22] Filed: Jun. 4, 1992

[30] Foreign Application Priority Data

Jun. 10, 1991 [DE] Fed. Rep. of Germany ....... 4119055

[51] Int. Cl.$^5$ .............................................. C07C 69/76
[52] U.S. Cl. ...................... 560/64; 562/401; 562/473
[58] Field of Search ............... 560/64; 562/473, 401

[56] References Cited

U.S. PATENT DOCUMENTS 4,582,857 4/1986 Grill et al. ................ 514/563

*Primary Examiner*—Paul J. Killos
*Attorney, Agent, or Firm*—Brumbaugh, Graves, Donohue & Raymond

[57] ABSTRACT

The preparation of the pure enantiomers of LIFIBROL and its alkyl esters is achieved with surprisingly good yield by reacting the pure enantiomeric forms of S(-) R(+)-4-(4-tert.butylphenyl)-1,2-epoxy butane with 4-hydroxybenzoic acid alkyl ester at elevated temperature in DMF and in the presence of 4-hydroxybenzoic acid alkyl ester sodium salt. Thereafter, the raw reaction product is separated. Either the stereochemically pure LIFIBROL ester is then recovered by recrystallization or the precipitated LIFIBROL enantiomer is made in pure crystalline form by mild alkaline saponification and subsequent acidification.

12 Claims, No Drawings

PROCESS FOR PREPARING THE PURE ENANTIOMERS OF LIFIBROL AND ITS ALKYL ESTERS

In EP 0 133 935 hypolipemically active p-oxybenzoic acid derivatives, processes for the preparation thereof and the use thereof as drugs are claimed. Of these highly effective and excellently compatible active substances, in therapeutical use in particular 4-[4-(4'-tert.butylphenyl)-2-hydroxybutoxy] benzoic acid (1) has proved it become known under the name LIFIBROL [INN].

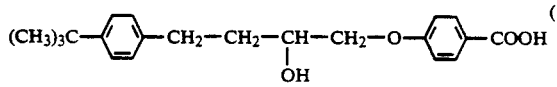

Since LIFIBROL has an asymmetry centre, in its preparation according to the process claimed it occurs in the form of an enantiomer mixture [(1a)+(1b)].

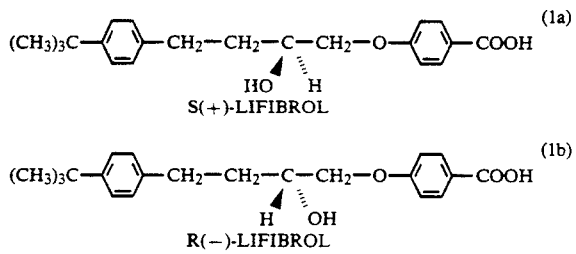

According to the present opinion on the proof of the efficacy and harmlessness of a new chiral active substance, it is essential to make the pure enantiomeric forms thereof available. As is known, enantiomers can differ clearly both in the bonding to proteins, in particular receptors, and in the kinetic and metabolic behaviour, and thus have very different pharmacological and toxicological effects. However, even with practically the same properties the pure enantiomer is to be preferred because the analysis is simplified compared with the racemate and a better control on the biological subject is possible.

In principle, only two processes are possible for recovering pure enantiomeric forms, either isolation from the racemate or asymmetrical synthesis.

An economic isolation from the racemate would appear to promise little chance of success because the asymmetry in the centre of the LIFIBROL molecule is not very pronounced and in a derivatisation of the enantiomer mixture to give the corresponding diastereomers only minor physico-chemical differences are to be expected. This also applies to the preparative separations in chiral columns.

However, it has been possible to find a synthesis process which permits the preparation of the pure enantiomers of LIFIBROL and its alkyl esters with a surprisingly good yield.

By reacting the pure enantiomeric forms of S(−) or R(+)-4-(4'-tert.butylphenyl)-1,2-epoxy butane with 4-hydroxybenzoic acid alkyl ester at elevated temperature in DMF and in the presence of 4-hydroxybenzoic acid alkyl ester sodium salt the stereochemically pure alkyl esters of LIFIBROL can be recovered with high yield and by weak alkaline saponification and subsequent acidification converted with good yield to the corresponding enantiomers.

The prestages necessary for the synthesis, such as S(−) or R(+)-4-(4'-tert.butylphenyl)-1,2-epoxy butane are obtained by reacting 4-tert.butylbenzyl magnesium chloride with commercially available stereochemically pure forms of glycidyltosylate or epichlorohydrin.

In the following examples the invention will be explained in detail.

EXAMPLE 1

R(−)-4[4-(4'-2-hydroxybutoxy] benzoic acid methyl ester 200 g (0.978 mol) R(+)-4-(4'-tert.butylphenyl)-1,2-epoxy butane are heated with 149 g (0.980 mol) 4-hydroxybenzoic acid methyl ester and 17.0 g (0.098 mol) 4-hydroxybenzoic acid methyl ester sodium salt in 660 ml dimethylformamide (DMF) for 5 hours whilst stirring to 125° C. Thereafter, the cooled mixture is poured into water, extracted twice with ethyl acetate and the combined organic phases are washed several times with 1 N NaOH and water. After drying over $Na_2SO_4$ the solvent is extracted in vacuum and a brown viscous residue obtained.

Raw yield 327 g (94%); colourless crystals of methylcyclohexane or methylcyclohexane/diisopropyl ether Melting point: 62°−64° C.

$[\alpha]_D^{20}: -9.5°[CH_2Cl_2, c\times 2]$.

$1_{H\text{-}NMR\text{-}Spectrum}$ (CDCl$_3$) :

1.31 s (9) (CH$_3$)$_3$C 1.70–2.07 m (2) ArCH$_2$CH$_2$ 2.44 d (1) OH 2.60–2.97 m (2) ArCH$_2$CH$_2$ 3.70–4.20 and 3.87 s(6) CH-CH$_2$O and OCH$_3$ 6.84–8.02 m (8) Aromate.

EXAMPLE 2

S(+)-4-[4-tert.butylphenyl)-2-hydroxybutoxy]-benzoic acid methyl ester 196 g (0.959 mol) S(−)-4-(4'-tert.butylphenyl)-1,2-epoxybutane are heated with 146 g (0.960mol) 4-hydroxybenzoic acid methyl ester and 16.7 g (0.096 mol) 4-hydroxybenzoic acid methyl ester sodium salt in 660 ml DMF for 5 hours whilst stirring to 125° C. and further processed as described in Example 1.

Raw yield 322.5 g (94%); colourless crystals of methylcyclohexane or methylcyclohexane/diisopropyl ether Melting point: 63°-64° C.

$[\alpha]_D^{20}: +10.75°$ $[CH_2Cl_2, c=2]$.

$1_{H-NMR-Spectrum}$ (CDCl$_3$) the R(−)-enantiomer.

EXAMPLE 3

R(−)-4-[4-(4'-tert.butylphenyl)-2-hydroxybutoxy] benzoic acid

R(−)-LIFIBROL 178 g (0.500 mol) raw R(−)-4-[4-(4'-tert.butylphenyl)-2-hydroxybutoxy] benzoic acid methyl ester prepared according to Example 1 are stirred with a solution of 66 g KOH in 425 ml methanol and 100 ml H$_2$O for 1 h and left to stand overnight. Thereafter, the mixture is poured into 2.25 l H$_2$O, extracted three times with tert.butylmethyl ether to remove neutral components and acidified with 100 ml conc. HCl. The precipitating product is picked up in ethyl acetate and the organic phase washed with water. After drying over Na$_2$SO$_4$ the solvent is extracted in vacuum and the residue crystallized from acetonitrile and methanol/H₂O (8:2).

Yield: 109.5 g (64%).
Melting point: 114°-117° C.
$[\alpha]_D^{20}$: −12.7° [CH₂Cl₂, c=2]
IR-Spectrum(KBr) (OH) 3600 bis 2400 cm⁻¹ (C=O) 1680 cm⁻¹
¹H-NMR-Spectrum (CDCl₃):
1.31 s (9) (CH₃)₃C
1.77-2.10 m (2) ArCH₂CH₂
2.60-3.00 m (2) ArCH₂CH₂
3.73-4.20 m (3) CHCH₂O
6.87-8.08 m (10) Aromate,OH, COOH.

EXAMPLE 4

S(+)-4-[4-(4'-tert.butylphenyl)-2hydroxybutoxy]-benzoic acid

S(+)-LIFIBROL 178 g (0.500 mol) raw S(+)-4-[4-(4'-tert.butylphenyl)-2-hydroxybutoxy]-benzoic acid prepared according to Example 2 are saponified and processed as described in Example 3.

Yield: 109 g (63%).
Melting point: 114°-116° C.
$[\alpha]_D^{20}$: +12.4° [CH₂Cl₂, c=2].
¹H-NMR-Spectrum (CDCl): identical to that of the R(−)-enantiomer.

PREPARATION OF THE PRECURSORS

EXAMPLE 5a

S(−)-4-(4'-tert.butylphenyl)-1,2-epoxybutane

The Grignard solution freshly prepared under argon from 16.5 g (0.679 g atom) magnesium chips and 118.0 g (0.650 mol) 4-tert.butylbenzyl chloride in 650 ml dry tetrahydrofuran (THF) is cooled to −20° C. Within 10 minutes, at −20° C. to −30° C. 120 ml dilithium tetrachlorocuprate solution (0.1 M in THF) is added dropwise and stirring continued for a further 15 min. before cooling to −55° C. To this mixture, at −50° to −55° a solution of 91.3 g (0.400 mol) S(+)-glycidyltosylate in 400 ml THF is added dropwise within 50 min and stirring continued when the addition is completed at the same temperature for 1.75 h. Thereafter, within 30 min a solvent mixture of 30 ml water and 100 ml THF is added dropwise and after removing the cooling bath stirring continued until the temperature has risen to −20°. Thereupon, 500 ml 15 percent NH₄Cl solution is stirred in, the organic phase separated and the aqueous phase extracted with tert.butylmethyl ether. The combined organic phases are washed with dilute NH₄Cl solution and dried over Na₂SO₄. After withdrawing the solvent in vacuum a ciscous yellow residue is obtained which is taken up in 300 ml methanol and filtered. The clear solution is mixed with 150 ml 20% sodium methanolate solution, stirred for 1.5 h at room temperature and poured into 1.6 l H₂O. The product is taken up in ethyl acetate, washed with water and dried over Na₂SO₄. After withdrawing the solvent in vacuum the raw product is subjected to a short-path distillation at 0.06 mbar and 60° to 65° C. Slightly yellowish oily liquid.

Yield: 77.3 g (94.6%).
$[\alpha]_D^{20}$: −12.0° (CH₂Cl₂, c=2).
¹H-NMR-Spectrum (CDCl₃):
1.33 s(9) (CH₃)₃C)
1.73-1.95 m (2) ArCH₂CH₂
2.45-3.08 m (5) ArCH₂CH₂,
7.25(centre) m (4) Aromate.

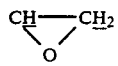

EXAMPLE 5b

S(−)-4-(4'-tert.butylphenyl)-1,2-epoxybutane

The Grignard solution freshly prepared from 12.5 g (0.514 g-atom) magnesium chips and 91.2 g (0.500 mol) 4-tert.butylbenzyl chloride in 500 ml dry THF under argon is cooled to −20° C. and mixed with 3.10 g (0.015 mol) copper(I) bromide-dimethyl sulfide complex. Stirring is carried out for 15 min at −25° to −30° C. After cooling to −65° C., within 30 min a solution of 68.4 g (0.300 mol) S(+)-glycidyltosylate in 300 ml THF is added dropwise and stirring continued at the same temperature after completion of the addition for 1.75 h. The further processing is as described in Example 5a. The raw product collecting (67.0 g) is purified chromatographically in a silica gel column with dichloromethane/petroleum ether (40°-60°)[8:2].

Yield: 54.0 G (88%).
$[\alpha]_D^{20}$: −12.8° (CH₂Cl₂, c=1).

EXAMPLE 6a

R(+)-4-(4'-tert.butylphenyl)-1,2-epoxybutane

The Grignard solution freshly prepared from 12.5 g (0.514 g-atom) magnesium chips and 91.2 g (0.500 mol) 4-tert.butylbenzyl chloride in 500 ml dry THF under argon is cooled to −20° C. and mixed with 100 ml dilithium tetrachlorocuprate solution [0.1 M in THF] and stirring continued for a further 15 min before cooling to −55° C. To this mixture, within 30 min. a solution of 68.4 g (0.300 mol) R(-)-glycidyltosylate in 300 ml THF is added dropwise and stirring continued at the same temperature after completion of the addition for 1.75 h. The further processing is as described in Example 5a.

Yield: 51.3 g (83%).
$[\alpha]_D^{20}$: +12.0° (CH₂Cl₂, c=1).
By chromatography with silica gel with CH₂Cl₂
Yield: 44.0 g (72%).
$[\alpha]_D^{20}$: +13.5° (CH₂Cl₂, c=1).
¹H-NMR-Spectrum (CDCl₃): identical to that of the S(−)-enantiomer.

EXAMPLE 6b

R(+)-4-(4'-tert.butylphenyl)-1,2-epoxybutane

The Grignard solution freshly prepared under argon from 38.9 g (1.60 g atom) magnesium chips and 292 g (1.60 mol) 4-tert.butylbenzyl chloride in 1600 ml dry THF is mixed with 92.5 g (1.00 mol) R(−)-epichlorohydrin in 300 ml THF within 1.5 h at 5 to 10° C. and stirring continued for a further 3 h without cooling. Thereupon, 400 ml 15% NH₄Cl solution are stirred in at 10 to 20° C., the organic phase separated and the aqueous phase extracted with 250 ml THF. The combined organic phases are washed with dilute NH₄Cl solution and dried over Na₂SO₄. After withdrawing the solvent in vacuum the residue is dissolved in 400 ml methanol, the filtered solution mixed with 330 ml of a 20% sodium methylate solution, stirred for 1.5 h at room temperature and poured into 1.6 l H₂O. The product is taken up in ethyl acetate, washed with water and dried over $Na_2SO_4$. After withdrawing the solvent in vacuum the raw product is subjected to a short-path distillation at 0.2 mbar and 60°–65° C.

Yield: 137.4 g (67%).

$[\alpha]_D^{20:}+13.4°$ ($CH_2Cl_2$, C=1.

Above, dimethylformamide was given as solvent. This solvent is preferably used. However, instead other solvents can also be employed, such as low alcohols with $C_1$–$C_4$ chains.

Furthermore, it was stated in the aforementioned examples of embodiment that the reaction is carried out in the presence of a small amount of alkali. The alkali is introduced in the form of a sodium salt of the respective hydroxybenzoic acid alkali ester. Instead of introducing a sodium salt in this manner, an alkali in the form of sodium hydroxide or potassium hydroxide may also be employed.

What is claimed is:

1. A process for preparing pure enantiomers of 4-[4-(4'-tert.butylphenyl)2-hydroxybutoxy]benzoic acid or of the alkyl esters thereof comprising the steps of:
    (a) reacting a single enantiomer of 4-(4'-tert.butyl-phenyl)-1,2-epoxybutane with an alkyl ester of 4-hydroxybenzoic acid in the presence of the sodium salt of the same 4-hydroxybenzoic acid ester at elevated temperature; and
    (b) recovering the resulting enantiomerically pure 4-[4-(4'-tert.butylphenyl)-2-hydroxybutoxy]benzoic acid or an alkyl ester thereof.

2. A process according to claim 1, wherein the enantiomerically pure product is recovered by recrystallization.

3. A process according to claim 1, wherein the enantiomercially pure product is recovered by performing a mild alkaline saponification followed by acidification to form a crystalline product.

4. Process according to claim 1, the methyl, ethyl or propyl ester of the 4-hydroxy benzoic acid is employed.

5. Process according to claim 1, the reaction is carried out in dimethylformamide at temperatures between 110 and 140° C.

6. Process according to claim 3, the saponification of the ester is carried out between 10° and 30° C.

7. A process for preparing pure enantiomers of 4-[4-(4'-tert.butylphenyl)-2-hydroxybutoxy] benzoic acid or the alkyl esters thereof comprising the steps of:
    (a) reacting a 4-tert.butylbenzyl magnesuim halide with a stereochemically pure glycydyl tosylate or epichlorohydrin to form a single enantiomer of 4-(4'-tert.butylphenyl)-1,2-epoxybutane;
    (b) separating the single enantiomer from the reaction mixture;
    (c) reacting the separated single enantiomer of 4-(4'-tert.butylphenyl)-1,2-epoxybutane with an alkyl ester of 4-hydroxybenzoic acid in the presence of the sodium salt of the same 4-hydroxybenzoic acid ester at elevated temperature; and
    (d) recovering the resulting enantiomerically pure 4-[4-4'-tert.butylphenyl)-2-hydroxybutoxy]benzoic acid or an alkyl ester thereof.

8. Process according to claim 7, wherein the methyl, ethyl or propyl ester of 4-hydroxybenzoic acid is employed.

9. Process according to claim 7, wherein the reaction of step C is carried out in dimethylformamide at temperature between 110° and 140 °.

10. Process according to claim 7, wherein the enantomerically pure product is recovered by recrystallization.

11. Process according to claim 7, wherein the enantiomerically pure product is recovered by performing a mild alkaline saponification followed by acidification to form a crystalline product.

12. Process according to claim 11, wherein the saponification is carried out between 10° and 30° C.

* * * * *

UNITED STATES PATENT AND TRADEMARK OFFICE
CERTIFICATE OF CORRECTION

PATENT NO. : 5,266,721

DATED : Nov. 30, 1993

INVENTOR(S) : Reiter et al.

It is certified that error appears in the above-identified patent and that said Letters Patent is hereby corrected as shown below:

On title page, item [57] Abstract, line 4, "R(+)-4-(4-tert." should read --R(+)-4-(4'-tert.--. Col. 1, line 12, "it" should read --itself and has--. Col. 2, line 12, "R(-)-4[4-(4'-2-hydroxybutoxy]" should read --R(-)-4-[4-(4'-tert.butylphenyl)-2-hydroxybutoxy]--; line 28, "c x 2" should read --c = 2--; line 38, "S(+)-4-[4-tert." should read --S(+)-4-[4-(4'-tert.--; line 51, "(CDCl$_3$) the" should read --(CDCl$_3$) : identical to the--. Col. 3, line 6, "(OH) 3600 bis 2400 cm$^{-1}$ (C=O)" should read --$\gamma$(OH) 3600 bis 2400 cm$^{-1}$ $\gamma$(C=O)--; line 16, "-2hydroxybutoxy" should read -- -2-hydroxybutoxy--; line 27, "(CDCl)" should read --(CDCl$_3$)--; line 54, "ciscous" should read --viscous--. Cols. 3 and 4, "CH - CH$_2$"

should appear at the end of line 68 in col. 3, instead of at line 5 in col. 4. Col. 5, line 5, "C=1" should read --c=1--; line 20, "(4'-tert.-butylphenyl)2-" should read --(4'-tert.butylphenyl)-2- --; bridging lines 33-34, "enantiomercially" should read --enantiomerically--; line 37, "the" should read --wherein the--.

UNITED STATES PATENT AND TRADEMARK OFFICE
CERTIFICATE OF CORRECTION

PATENT NO. : 5,266,721

DATED : Nov. 30, 1993

INVENTOR(S) : Reiter et al.

It is certified that error appears in the above-identified patent and that said Letters Patent is hereby corrected as shown below:

<u>Col. 6, line 1</u>, "the" should read --wherein the--; <u>line 4</u>, "the" should read --wherein the--; <u>line 9</u>, "magnesuim" should read --magnesium--, <u>bridging lines 29-30</u>, "enantomerically" should read --enanhomerically--

Signed and Sealed this

Fifth Day of July, 1994

Attest:

BRUCE LEHMAN

*Attesting Officer*  *Commissioner of Patents and Trademarks*

UNITED STATES PATENT AND TRADEMARK OFFICE
CERTIFICATE OF CORRECTION

PATENT NO. : 5,266,721

DATED : Nov. 30, 1993

INVENTOR(S) : Reiter et al.

It is certified that error appears in the above-identified patent and that said Letters Patent is hereby corrected as shown below:

On title page, item [57] Abstract, line 4, "R(+)-4-(4-tert." should read --R(+)-4-(4'-tert.--. <u>Col. 1, line 12</u>, "it" should read --itself and has--. <u>Col. 2, line 12</u>, "R(-)-4[4-(4'-2-hydroxybutoxy]" should read --R(-)-4-[4-(4'-tert.butylphenyl)-2-hydroxybutoxy]--; <u>line 28</u>, "c x 2" should read --c = 2--; <u>line 38</u>, "S(+)-4-[4-tert." should read --S(+)-4-[4-(4'-tert.--; <u>line 51</u>, "(CDCl$_3$) the" should read --(CDCl$_3$) : identical to the--. <u>Col. 3, line 6</u>, "(OH) 3600 bis 2400 cm$^{-1}$ (C=O)" should read --γ(OH) 3600 bis 2400 cm$^{-1}$ γ(C=O)--; <u>line 16</u>, "-2hydroxybutoxy" should read -- -2-hydroxybutoxy--; <u>line 27</u>, "(CDCl)" should read --(CDCl$_3$)--; <u>line 54</u>, "ciscous" should read --viscous--. <u>Cols. 3 and 4</u>, "CH - CH$_2$" 

should appear at the end of line 68 in col. 3, instead of at line 5 in col. 4. <u>Col. 5, line 5</u>, "C=1" should read --c=1--; <u>line 20</u>, "(4'-tert.-butylphenyl)2-" should read --(4'-tert.butylphenyl)-2- --; <u>bridging lines 33-34</u>, "enantiomercially" should read --enantiomerically--; <u>line 37</u>, "the" should read --wherein the--.

This certificate supercedes certificate of Correction of Correction issued July 5, 1994

UNITED STATES PATENT AND TRADEMARK OFFICE
CERTIFICATE OF CORRECTION

PATENT NO. : 5,266,721
DATED : Nov. 30, 1993
INVENTOR(S) : Reiter et al.

It is certified that error appears in the above-identified patent and that said Letters Patent is hereby corrected as shown below:

Col. 6, line 1, "the" should read --wherein the--; line 4, "the" should read --wherein the--; line 9, "magnesuim" should read --magnesium--, bridging lines 29-30, "enantomerically" should read -- enantomerically --.

Signed and Sealed this

Twenty-seventh Day of September, 1994

Attest:

BRUCE LEHMAN

Attesting Officer

Commissioner of Patents and Trademarks